United States Patent
Hoshiya et al.

(10) Patent No.: US 11,932,596 B2
(45) Date of Patent: *Mar. 19, 2024

(54) FLUOROVINYL ETHER COMPOUND

(71) Applicant: DAIKIN INDUSTRIES, LTD., Osaka (JP)

(72) Inventors: Naoyuki Hoshiya, Osaka (JP); Akihiro Gotou, Osaka (JP); Yosuke Kishikawa, Osaka (JP)

(73) Assignee: DAIKIN INDUSTRIES, LTD., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 18/091,516

(22) Filed: Dec. 30, 2022

(65) Prior Publication Data

US 2023/0144907 A1     May 11, 2023

Related U.S. Application Data

(62) Division of application No. 17/255,689, filed as application No. PCT/JP2019/025477 on Jun. 26, 2019, now Pat. No. 11,560,347.

(30) Foreign Application Priority Data

Jun. 26, 2018  (JP) ................. 2018-120779

(51) Int. Cl.
  *C07C 43/176*   (2006.01)
  *C07C 41/16*   (2006.01)
  (Continued)

(52) U.S. Cl.
  CPC .............. *C07C 41/16* (2013.01); *C07C 43/17* (2013.01); *C07C 43/176* (2013.01);
  (Continued)

(58) Field of Classification Search
  CPC ..... C07C 43/17; C07C 43/176; C07D 209/48; C07D 213/30; C07D 317/22; C07D 333/16; C07D 211/22; C07F 7/1804
  See application file for complete search history.

(56) References Cited

U.S. PATENT DOCUMENTS 2,799,712 A   7/1957  Speers et al.
5,847,166 A   12/1998 Buchwald et al.
(Continued)

FOREIGN PATENT DOCUMENTS

GB    782477    9/1957
JP    2010-229049  10/2010
(Continued)

OTHER PUBLICATIONS

Muzalevskiy et al., "Synthetic Approach to Alkoxy-β-(trifluoromethyl)styrenes and Their Application in the Synthesis of New Trifluoromethylated lated Heterocycles", Synthesis, 2009, vol. 13, pp. 2249-2259.

(Continued)

*Primary Examiner* — Rosalynd A Keys
(74) *Attorney, Agent, or Firm* — Wenderoth, Lind & Ponack, L.L.P.

(57) ABSTRACT

An object of the present invention is to provide, for example, a novel method for synthesizing a fluorovinyl ether compound from a fluorine-containing vinyl compound. This problem is solved by a method for producing a compound represented by formula (1):

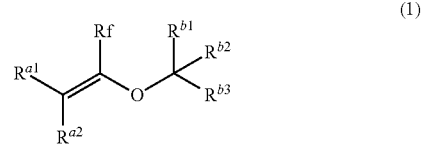

(1)

wherein
$R^{a1}$ is a hydrogen atom, a halogeno group, an alkyl group, a fluoroalkyl group, or an aromatic group optionally having one or more substituents,
Rf is a fluoro group or a perfluoroalkyl group,
$R^{a2}$ is a hydrogen atom, a halogeno group, an alkyl group, a fluoroalkyl group, or an aromatic group optionally having one or more substituents, or
(i) $R^{a1}$ and $R^{a2}$, (ii) $R^{a1}$ and Rf, or (iii) Rf and $R^{a2}$ may be linked to each other,
$R^{b1}$ is $R^s$,
$R^{b2}$ is a hydrogen atom or $R^s$,
$R^{b3}$ is a hydrogen atom or $R^s$, or
two or three of $R^{b1}$, $R^{b2}$, and $R^{b3}$, taken together with the adjacent carbon atom, may form a ring optionally having one or more substituents, and
$R^s$, in each occurrence, is the same or different and represents a hydrocarbon group optionally having one or more substituents, the method comprising
step A of reacting a compound represented by formula (2):

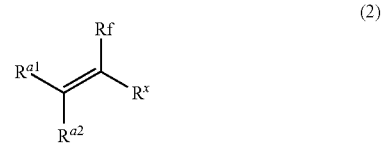

(2)

wherein
$R^x$ is a leaving group, and
other symbols are as defined above,
with a compound represented by formula (3):

(Continued)

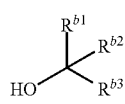

(3)

wherein the symbols in the formula are as defined above, in the presence of a transition metal catalyst.

6 Claims, No Drawings

(51) Int. Cl.
  *C07C 43/17* (2006.01)
  *C07D 209/48* (2006.01)
  *C07D 211/22* (2006.01)
  *C07D 213/30* (2006.01)
  *C07D 317/22* (2006.01)
  *C07D 333/16* (2006.01)
  *C07F 7/18* (2006.01)

(52) U.S. Cl.
  CPC .......... *C07D 209/48* (2013.01); *C07D 211/22* (2013.01); *C07D 213/30* (2013.01); *C07D 317/22* (2013.01); *C07D 333/16* (2013.01); *C07F 7/1804* (2013.01)

(56) References Cited

U.S. PATENT DOCUMENTS

| 11,560,347 | B2* | 1/2023 | Hoshiya ............... C07D 317/22 |
| 2001/0008942 | A1 | 7/2001 | Buchwald et al. |
| 2003/0083529 | A1 | 5/2003 | Ishii et al. |
| 2010/0249465 | A1 | 9/2010 | Tenjimbayashi et al. |
| 2015/0191413 | A1 | 7/2015 | Ohtsuka et al. |

FOREIGN PATENT DOCUMENTS

| JP | 2013-18744 | 1/2013 |
| JP | 2014-62092 | 4/2014 |
| JP | 2014-73980 | 4/2014 |
| JP | 2015-143199 | 8/2015 |
| JP | 2015-168650 | 9/2015 |

OTHER PUBLICATIONS

Muzalevskiy et al., "Synthesis of Trifluoromethyl alcohols from tert-butoxy-β-(trifluormethyl) styrenes and trifluoromethylbenzyl ketones under the conditions of the leuckart-Wallach reaction", Journal of Fluorine Chemistry, 2008, vol. 129, pp. 1052-1055.
Goldberg et al., "Novel efficient synthesis of β-fluoro-β-(trifluoromethyl)styrenes", Journal of Fluorine Chemistry, 2010, vol. 131, pp. 384-388.
Sokolenko et al. "Polyfluoroalkylation and Alkenylation of 1-Benzyl-1H-Indazol-3-OL", Chemistry of Heterocyclic Compounds, 2011, vol. 46, No. 11, pp. 1335-1343.
Klein et al., "Synthesis, radiolabeling and preclinical evaluation of a [$^{11}$C]GMOM derivative as PET radiotracer for the ion channel of the N-methyl-D-aspartate receptor", Nuclear Medicine and Biology, 2017, vol. 51, pp. 25-32.
International Search Report dated Sep. 10, 2019 in International (PCT) Patent Application No. PCT/JP2019/025477.
Murata, Junji et al., "Selective synthesis of fluorinated ethers by addition reaction of alcohols to fluorinated olefins in water", Green Chemistry, 2002, vol. 4, pp. 60-63.
Extended European Search Report dated Feb. 8, 2022 in corresponding European Patent Application No. 19825282.7.
Matsukawa, Yasuhisa et al., "Palladium(0)-Catalyzed Hydroalkoxylation of Hexafluoropropene: Synthesis of Hydrofluoroethers under Neutral Conditions", Angew. Chem. Int. Ed., 2005, vol. 44, No. 7, pp. 1128-1130.
Koshar, Robert J. et al., "The Addition of Alcohols to Octafluoroisobutene", J. Am. Chem. Soc., vol. 79, No. 7, 1957, pp. 1741-1744.
Koch, H. F. et al., "Proton-Transfer Reactions. 1. Partitioning of Carbanion Intermediates Generated by Reactions of Alkenes with Alkoxide Ions in Alcohol", J. Am. Chem. Soc., vol. 103, No. 18, 1981, pp. 5417-5423.

* cited by examiner

FLUOROVINYL ETHER COMPOUND

TECHNICAL FIELD

The present invention relates to a method for producing a fluorovinyl ether compound.

BACKGROUND ART

Examples of conventionally known methods for synthesizing fluorovinyl ethers include substitution reaction of a fluorine-containing vinyl compound using a strong base (e.g., Patent Literature (PTL) 1, Non-patent Literature (NPL) 1, and NPL 2).

However, a method for synthesizing a fluorovinyl ether from a fluorine-containing vinyl compound at a high yield has not yet been reported.

CITATION LIST

Patent Literature

PTL 1: U.S. Pat. No. 2,799,712

Non-Patent Literature

NPL 1: T. M. Sokolenko et al., Chemistry of Heterocyclic Compounds, 2011, 46: 1335

NPL 2: Pieter J. Klein et al., Nuclear Medicine and Biology, 2017, vol. 51, pp. 25-32

SUMMARY OF INVENTION

Technical Problem

An object of the present invention is to provide a novel method for synthesizing a fluorovinyl ether compound from a fluorine-containing vinyl compound.

Solution to Problem

As a result of extensive research, the present inventors found that the above problem can be solved by a method for producing a compound represented by formula (1):

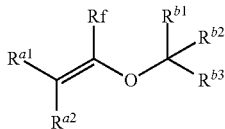

wherein
$R^{a1}$ is a hydrogen atom, a halogeno group, an alkyl group, a fluoroalkyl group, or an aromatic group optionally having one or more substituents,
Rf is a fluoro group or a perfluoroalkyl group,
$R^{a2}$ is a hydrogen atom, a halogeno group, an alkyl group, a fluoroalkyl group, or an aromatic group optionally having one or more substituents, or
(i) $R^{a1}$ and $R^{a2}$, (ii) $R^{a1}$ and Rf, or (iii) Rf and $R^{a2}$ may be linked to each other,
$R^{b1}$ is $R^s$,
$R^{b2}$ is a hydrogen atom or $R^s$,
$R^{b3}$ is a hydrogen atom or $R^s$, or
two or three of $R^{b1}$, $R^{b2}$, and $R^{b3}$, taken together with the adjacent carbon atom, may form a ring optionally having one or more substituents, and
$R^s$, in each occurrence, is the same or different and represents a hydrocarbon group optionally having one or more substituents, the method comprising
step A of reacting a compound represented by formula (2):

wherein
$R^x$ is a leaving group, and
other symbols are as defined above,
with a compound represented by formula (3):

wherein the symbols in the formula are as defined above, in the presence of a transition metal catalyst.

The present invention has thus been accomplished.

The present invention includes the following embodiments.

Item 1. A method for producing a compound represented by formula (1):

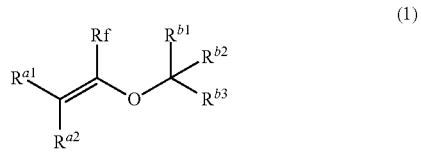

wherein
$R^{a1}$ is a hydrogen atom, a halogeno group, an alkyl group, a fluoroalkyl group, or an aromatic group optionally having one or more substituents,
Rf is a fluoro group or a perfluoroalkyl group,
$R^{a2}$ is a hydrogen atom, a halogeno group, an alkyl group, a fluoroalkyl group, or an aromatic group optionally having one or more substituents, or
(i) $R^{a1}$ and $R^{a2}$, (ii) $R^{a1}$ and Rf, or (iii) Rf and $R^{a2}$ may be linked to each other,
$R^{b1}$ is $R^s$,
$R^{b2}$ is a hydrogen atom or $R^s$,
$R^{b3}$ is a hydrogen atom or $R^s$, or
two or three of $R^{b1}$, $R^{b2}$, and $R^{b3}$, taken together with the adjacent carbon atom, may form a ring optionally having one or more substituents, and
$R^s$, in each occurrence, is the same or different and represents a hydrocarbon group optionally having one or more substituents, the method comprising step A of reacting a compound represented by formula (2):

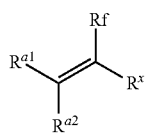
(2)

wherein
$R^x$ is a leaving group, and
other symbols are as defined above,
with a compound represented by formula (3):

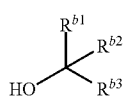
(3)

wherein the symbols in the formula are as defined above,
in the presence of a transition metal catalyst.

Item 2. The production method according to Item 1, wherein $R^{a1}$ is a hydrogen atom.

Item 3. The production method according to Item 1 or 2, wherein $R^{a2}$ is a hydrogen atom or an aryl group.

Item 4. The production method according to any one of Items 1 to 3, wherein $R^{b1}$ is a $C_{1\text{-}11}$ fluoroalkyl group, $R^{b2}$ is a hydrogen atom, and $R^b3$ is a hydrogen atom.

Item 5. The production method according to Item 4, wherein $R^{b1}$ is a $C_{1\text{-}11}$ perfluoroalkyl group.

Item 6. The production method according to any one of Items 1 to 5, wherein $R^x$ is a halogeno group or a sulfonic acid ester group.

Item 7. The production method according to any one of Items 1 to 6, wherein the transition metal catalyst is at least one member selected from the group consisting of palladium catalysts, copper catalysts, nickel catalysts, platinum catalysts, and iron catalysts.

Item 8. The production method according to Item 7, wherein the transition metal catalyst is a palladium complex.

Item 9. The production method according to any one of Items 1 to 8, wherein the reaction of step A is performed in the presence of a coordination compound.

Item 10. The production method according to Item 9, wherein the coordination compound is a biphenyl compound represented by formula (4-1):

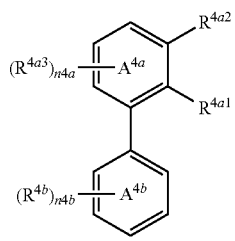
(4-1)

wherein
$A^4a$ is a benzene ring,
$A^{4b}$ is a benzene ring,
$R^{4a1}$ is a phosphino group substituted with two $C_{1\text{-}20}$ hydrocarbon groups, $R^{4a2}$ is an alkyl group or an alkoxy group,
$R^{4a3}$, in each occurrence, is the same or different and represents a substituent,
$R^{4b}$, in each occurrence, is the same or different and represents a substituent,
n4a is a number of 0 to 3, and
n4b is a number of 0 to 5.

Item 11. The production method according to Item 10, wherein $R^{4a1}$ is a phosphino group substituted with two substituents selected from the group consisting of cyclohexyl, tert-butyl, and adamantyl groups, and $R^{4a2}$ is a methyl group or a methoxy group.

Item 12. The production method according to any one of Items 1 to 11, wherein the reaction of step A is performed in the presence of a base.

Item 13. The production method according to Item 12, wherein the base has a pKa of 36 to 3.6.

Item 14. The production method according to Item 12, wherein the base is at least one member selected from the group consisting of
(1) acetates, carbonates, hydrogen carbonates, phosphates, hydrogen phosphates, alkoxide salts, hydroxide salts, hydride salts, ammonium salts, and amide salts of alkaline or alkaline earth metals,
(2) polymer-supported bases,
(3) alkali metals, and
(4) amines.

Item 15. A compound represented by formula (1-1):

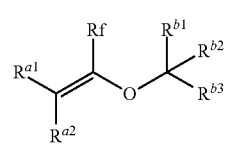
(1-1)

wherein
Rf is a fluoro group or a perfluoroalkyl group,
$R^{a1}$ is a hydrogen atom,
$R^{a2}$ is a hydrogen atom,
$R^{b1}$ is a hydrogen atom,
$R^{b2}$ is a hydrogen atom, and
$R^{b3}$ is a $C_{2\text{-}11}$ fluoroalkyl group or a $C_{3\text{-}11}$ perfluoroalkylpolyether group.

Item 16. A compound represented by formula (1-2):

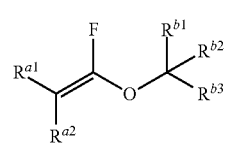
(1-2)

wherein
$R^{a1}$ is a hydrogen atom,
$R^{a2}$ is an aryl group or a heterocyclic group,
$R^{b1}$ is a hydrogen atom,
$R^{b2}$ is a hydrogen atom, and
$R^{b3}$ is a $C_{1\text{-}11}$ fluoroalkyl group.

Advantageous Effects of Invention

The present invention provides, for example, a method for synthesizing a fluorovinyl ether compound from a fluorine-containing vinyl compound at a high yield.

DESCRIPTION OF EMBODIMENTS

Terms

Symbols and abbreviations in the present specification can be understood as indicating the meanings typically used in the technical field to which the present invention pertains in accordance with the context of the specification, unless otherwise specified.

In the present specification, the terms "comprise" and "contain" are used with the intention of including the phrases "consist essentially of" and "consist of."

Unless otherwise specified, the steps, treatments, or operations described in the present specification may be performed at room temperature.

In the present specification, room temperature can refer to a temperature in the range of 10 to 40° C.

In the present specification, the term "Cn-m" (wherein n and m each represent a number) indicates that the number of carbon atoms is n or more and m or less, as a person skilled in the art would usually understand.

In the present specification, unless otherwise specified, examples of "halogen atom" include fluorine, chlorine, iodine, and bromine.

In the present specification, unless otherwise specified, the term "halogeno group" includes fluoro, chloro, bromo, and iodo.

In the present specification, unless otherwise specified, the term "organic group" refers to a group formed by removing one hydrogen atom from an organic compound. As can be understood from this, an organic group contains one or more carbon atoms.

In the present specification, unless otherwise specified, the term "organic group" includes
(1) hydrocarbon groups and
(2) hydrocarbon groups having one or more heteroatoms (e.g., nitrogen, oxygen, sulfur, phosphorus, halogen).

In the present specification, unless otherwise specified, the term "hydrocarbon group" refers to a group consisting only of carbon and hydrogen.

A hydrocarbon group can also be called a hydrocarbyl group.

In the present specification, unless otherwise specified, example of "hydrocarbon group" include
(1) aliphatic hydrocarbon groups optionally substituted with one or more aromatic hydrocarbon groups (e.g., benzyl group), and
(2) aromatic hydrocarbon groups optionally substituted with one or more aliphatic hydrocarbon groups.

An aromatic hydrocarbon group can also be called an aryl group.

In the present specification, unless otherwise specified, the "aliphatic hydrocarbon group" can have a linear, branched, or cyclic structure; or a combination thereof.

In the present specification, unless otherwise specified, the "aliphatic hydrocarbon group" may be saturated or unsaturated.

In the present specification, unless otherwise specified, examples of the "aliphatic hydrocarbon group" include alkyl groups, alkenyl groups, alkynyl groups, and cycloalkyl groups.

In the present specification, unless otherwise specified, the "alkyl (group)" may have a linear or branched structure, or a combination thereof.

In the present specification, unless otherwise specified, examples of "alkyl (group)" include $C_{1-11}$ linear or branched alkyl groups. Specific examples include methyl, ethyl, propyl (e.g., n-propyl, isopropyl), butyl (e.g., n-butyl, isobutyl, sec-butyl, tert-butyl), pentyl (e.g., n-pentyl, tert-pentyl, neopentyl, isopentyl, sec-pentyl, 3-pentyl), hexyl, heptyl, octyl, nonyl, and decyl.

In the present specification, unless otherwise specified, examples of "alkenyl (group)" include linear or branched alkenyl groups having 1 to 10 carbon atoms. Specific examples include vinyl, 1-propenyl, isopropenyl, 2-methyl-1-propenyl, 1-butenyl, 2-butenyl, 3-butenyl, 2-ethyl-1-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl, and 5-hexenyl.

In the present specification, unless otherwise specified, examples of "alkynyl (group)" include linear or branched alkynyl groups having 2 to 6 carbon atoms. Specific examples include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, and 5-hexynyl.

In the present specification, unless otherwise specified, examples of "cycloalkyl (group)" include cycloalkyl groups having 3 to 10 carbon atoms. Specific examples include cyclopropyl, cyclobutyl, cyclopentyl, cyclohexyl, cycloheptyl, cyclooctyl, and adamantyl.

In the present specification, unless otherwise specified, examples of "aromatic hydrocarbon group (aryl (group))" include $C_{6-14}$ aromatic hydrocarbon groups (aryl group). Specific examples include phenyl, naphthyl, phenanthryl, anthryl, and pyrenyl.

In the present specification, unless otherwise specified, examples of "aromatic hydrocarbon ring" include $C_{6-14}$ aromatic hydrocarbon rings. Specific examples includes a benzene ring, a naphthalene ring, an anthracene ring, and a phenanthrene ring.

In the present specification, unless otherwise specified, the term "alkoxy (group)" may refer to a group represented by RO— (wherein R is an alkyl group (e.g., a $C_{1-11}$ alkyl group)). Examples include $C_{1-11}$ alkoxy groups (e.g., methoxy, ethoxy, propoxy, isopropoxy, n-butoxy, isobutoxy, sec-butoxy, pentyloxy, and hexyloxy).

In the present specification, unless otherwise specified, the term "alkylcarbonyloxy (group)" may refer to a group represented by RCO—O— (wherein R is an alkyl group).

Specific examples include an acetoxy group.

In the present specification, unless otherwise specified, the term "ester group" refers to an organic group having at least one ester bond (i.e., —C(=O)—O— or —O—C(=O)—).

Examples of the "ester group" include
(1) groups represented by the formula: $RCO_2$— (wherein R is an alkyl group), and
(2) groups represented by the formula: $R^a$—$CO_2$—$R^b$— (wherein $R^a$ is an alkyl group, and $R^b$ is an alkylene group).

In the present specification, unless otherwise specified, the term "ether group" refers to a group having one or more ether bonds (—O—).

Examples of the "ether group" include polyether groups.

In the present specification, unless otherwise specified, the term "polyether group" refers to a group having two or more (e.g., 2, 3, 4, 5, 6, 7, 8, or 9) ether bonds (—O—).

Examples of polyether groups include groups represented by the formula: $R^a$—(O—$R^b$)$_n$— (wherein $R^a$ is an alkyl group, $R^b$, in each occurrence, is the same or different and represents an alkylene group, and n is an integer of 1 or more).

An alkylene group refers to a divalent group formed by removing one hydrogen atom from the alkyl group mentioned above.

Examples of the "ether group" also include hydrocarbyl ether groups.

The term "hydrocarbyl ether group" refers to a hydrocarbon group having one or more ether bonds.

The "hydrocarbyl group having one or more ether bonds" may be a hydrocarbyl group having one or more ether bonds internally or at the end of the group.

Examples include alkoxy groups and benzyloxy groups.

Examples of the "hydrocarbon group having one or more ether bonds" include alkyl groups having one or more ether bonds.

The "alkyl group having one or more ether bonds" may be an alkyl group into which one or more ether bonds are inserted.

Such a group may also be called an alkyl ether group.

In the present specification, the prefix "perfluoro" can mean that all hydrogen are replaced by fluoro, as can be typically understood by a person skilled in the art.

In the present specification, unless otherwise specified, the term "acyl (group)" includes alkanoyl groups.

In the present specification, unless otherwise specified, the "alkanoyl group" refers to, for example, a group represented by RCO— (wherein R is an alkyl group).

Specific examples include acetyl.

In the present specification, unless otherwise specified, the term "cyclic group" includes cyclic aliphatic hydrocarbon groups (e.g., cycloalkyl), aromatic hydrocarbon groups (aryl), and heterocyclic groups.

In the present specification, unless otherwise specified, the term "heterocyclic group" includes non-aromatic heterocyclic groups and heteroaryl groups.

In the present specification, examples of "heterocyclic group" include 5- to 18-membered heterocyclic groups.

In the present specification, examples of "heterocyclic group" include 5- to 10-membered heterocyclic groups.

In the present specification, unless otherwise specified, a "heterocyclic group" may be monocyclic, bicyclic, tricyclic, or tetracyclic.

In the present specification, unless otherwise specified, the "heterocyclic group" may be, for example, a heterocyclic group containing, in addition to carbon, 1 to 4 heteroatoms selected from the group consisting of oxygen, sulfur, and nitrogen as a ring-constituting atom or ring-constituting atoms.

In the present specification, unless otherwise specified, the "non-aromatic heterocyclic group" may be saturated or unsaturated.

In the present specification, unless otherwise specified, examples of "non-aromatic heterocyclic group" include tetrahydrofuryl, oxazolidinyl, imidazolinyl (e.g., 1-imidazolinyl, 2-imidazolinyl, and 4-imidazolinyl), aziridinyl (e.g., 1-aziridinyl and 2-aziridinyl), azetidinyl (e.g., 1-azetidinyl and 2-azetidinyl), pyrrolidinyl (e.g., 1-pyrrolidinyl, 2-pyrrolidinyl, and 3-pyrrolidinyl), piperidinyl (e.g., 1-piperidinyl, 2-piperidinyl, and 3-piperidinyl), azepanyl (e.g., 1-azepanyl, 2-azepanyl, 3-azepanyl, and 4-azepanyl), azocanyl (e.g., 1-azocanyl, 2-azocanyl, 3-azocanyl, and 4-azocanyl), piperazinyl (e.g., 1,4-piperazin-1-yl and 1,4-piperazin-2-yl), diazepinyl (e.g., 1,4-diazepin-1-yl, 1,4-diazepin-2-yl, 1,4-diazepin-5-yl, and 1,4-diazepin-6-yl), diazocanyl (e.g., 1,4-diazocan-1-yl, 1,4-diazocan-2-yl, 1,4-diazocan-5-yl, 1,4-diazocan-6-yl, 1,5-diazocan-1-yl, 1,5-diazocan-2-yl, and 1,5-diazocan-3-yl), tetrahydropyranyl (e.g., tetrahydropyran-4-yl), morpholinyl (e.g., 4-morpholinyl), thiomorpholinyl (e.g., 4-thiomorpholinyl), 2-oxazolidinyl, dihydrofuryl, dihydropyranyl, and dihydroquinolyl.

In the present specification, unless otherwise specified, examples of "heteroaryl (group)" include monocyclic aromatic heterocyclic groups (e.g., 5- or 6-membered monocyclic aromatic heterocyclic groups), and aromatic fused heterocyclic groups (e.g., 5- to 18-membered aromatic fused heterocyclic groups).

In the present specification, unless otherwise specified, examples of "5- or 6-membered monocyclic aromatic heterocyclic group" include pyrrolyl (e.g., 1-pyrrolyl, 2-pyrrolyl, and 3-pyrrolyl), furyl (e.g., 2-furyl and 3-furyl), thienyl (e.g., 2-thienyl and 3-thienyl), pyrazolyl (e.g., 1-pyrazolyl, 3-pyrazolyl, and 4-pyrazolyl), imidazolyl (e.g., 1-imidazolyl, 2-imidazolyl, and 4-imidazolyl), isoxazolyl (e.g., 3-isoxazolyl, 4-isoxazolyl, and 5-isoxazolyl), oxazolyl (e.g., 2-oxazolyl, 4-oxazolyl, and 5-oxazolyl), isothiazolyl (e.g., 3-isothiazolyl, 4-isothiazolyl, and 5-isothiazolyl), thiazolyl (e.g., 2-thiazolyl, 4-thiazolyl, and 5-thiazolyl), triazolyl (e.g., 1,2,3-triazol-4-yl and 1,2,4-triazol-3-yl), oxadiazolyl (e.g., 1,2,4-oxadiazol-3-yl and 1,2,4-oxadiazol-5-yl), thiadiazolyl (e.g., 1,2,4-thiadiazol-3-yl and 1,2,4-thiadiazol-5-yl), tetrazolyl, pyridyl (e.g., 2-pyridyl, 3-pyridyl, and 4-pyridyl), pyridazinyl (e.g., 3-pyridazinyl and 4-pyridazinyl), pyrimidinyl (e.g., 2-pyrimidinyl, 4-pyrimidinyl, and 5-pyrimidinyl), and pyrazinyl.

In the present specification, unless otherwise specified, examples of "5- to 18-membered aromatic fused heterocyclic group" include isoindolyl (e.g., 1-isoindolyl, 2-isoindolyl, 3-isoindolyl, 4-isoindolyl, 5-isoindolyl, 6-isoindolyl, and 7-isoindolyl), indolyl (e.g., 1-indolyl, 2-indolyl, 3-indolyl, 4-indolyl, 5-indolyl, 6-indolyl, and 7-indolyl), benzo[b]furanyl (e.g., 2-benzo[b]furanyl, 3-benzo[b]furanyl, 4-benzo[b]furanyl, 5-benzo[b]furanyl, 6-benzo[b]furanyl, and 7-benzo[b]furanyl), benzo[c]furanyl (e.g., 1-benzo[c]furanyl, 4-benzo[c]furanyl, and 5-benzo[c]furanyl), benzo[b]thienyl (e.g., 2-benzo[b]thienyl, 3-benzo[b]thienyl, 4-benzo[b]thienyl, 5-benzo[b]thienyl, 6-benzo[b]thienyl, and 7-benzo[b]thienyl), benzo[c]thienyl (e.g., 1-benzo[c]thienyl, 4-benzo[c]thienyl, and 5-benzo[c]thienyl), indazolyl (e.g., 1-indazolyl, 2-indazolyl, 3-indazolyl, 4-indazolyl, 5-indazolyl, 6-indazolyl, and 7-indazolyl), benzimidazolyl (e.g., 1-benzimidazolyl, 2-benzimidazolyl, 4-benzimidazolyl, and 5-benzimidazolyl), 1,2-benzisoxazolyl (e.g., 1,2-benzisoxazol-3-yl, 1,2-benzisoxazol-4-yl, 1,2-benzisoxazol-5-yl, 1,2-benzisoxazol-6-yl, and 1,2-benzisoxazol-7-yl), benzoxazolyl (e.g., 2-benzoxazolyl, 4-benzoxazolyl, 5-benzoxazolyl, 6-benzoxazolyl, and 7-benzoxazolyl), 1,2-benzisothiazolyl (e.g., 1,2-benzisothiazol-3-yl, 1,2-benzisothiazol-4-yl, 1,2-benzisothiazol-5-yl, 1,2-benzisothiazol-6-yl, and 1,2-benzisothiazol-7-yl), benzothiazolyl (e.g., 2-benzothiazolyl, 4-benzothiazolyl, 5-benzothiazolyl, 6-benzothiazolyl, and 7-benzothiazolyl), isoquinolyl (e.g., 1-isoquinolyl, 3-isoquinolyl, 4-isoquinolyl, and 5-isoquinolyl), quinolyl (e.g., 2-quinolyl, 3-quinolyl, 4-quinolyl, 5-quinolyl, and 8-quinolyl), cinnolinyl (e.g., 3-cinnolinyl, 4-cinnolinyl, 5-cinnolinyl, 6-cinnolinyl, 7-cinnolinyl, and 8-cinnolinyl), phthalazinyl (e.g., 1-phthalazinyl, 4-phthalazinyl, 5-phthalazinyl, 6-phthalazinyl, 7-phthalazinyl, and 8-phthalazinyl), quinazolinyl (e.g., 2-quinazolinyl, 4-quinazolinyl, 5-quinazolinyl, 6-quinazolinyl, 7-quinazolinyl, and 8-quinazolinyl), quinoxalinyl (e.g., 2-quinoxalinyl, 3-quinoxalinyl, 5-quinoxalinyl, 6-quinoxalinyl, 7-quinoxalinyl, and 8-quinoxalinyl), pyrazolo[1,5-a]pyridyl (e.g., pyrazolo[1,5-a]pyridin-2-yl, pyrazolo[1,5-a]pyridin-3-yl, pyrazolo[1,5-a]pyridin-4-yl, pyrazolo[1,5-a]pyridin-5-yl, pyrazolo[1,5-a]pyridin-6-yl, and pyrazolo[1,5-a]pyridin-7-yl), and imidazo[1,2-a]pyridyl (e.g., imidazo[1,2-a]pyridin-2-yl, imidazo[1,2-a]pyridin-3-yl, imidazo[1,2-a]pyridin-5-yl, imidazo[1,2-a]pyridin-6-yl, imidazo[1,2-a]pyridin-7-yl, and imidazo[1,2-a]pyridin-8-yl).

In the present specification, examples of "aromatic group" include aryl groups, and aromatic heterocyclic groups.

1. Production Method

The production method of the present invention is a method for producing a compound represented by formula (1):

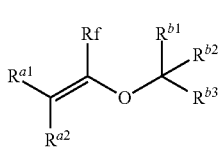

(1)

wherein
Rf is a fluoro group or a perfluoroalkyl group,
$R^{a1}$ is a hydrogen atom, a halogeno group, an alkyl group, a fluoroalkyl group, or an aromatic group optionally having one or more substituents,
$R^{a2}$ is a hydrogen atom, a halogeno group, an alkyl group, a fluoroalkyl group, or an aromatic group optionally having one or more substituents, or
(i) $R^{a1}$ and $R^{a2}$, (ii) $R^{a1}$ and Rf, or (iii) Rf and $R^{a2}$ may be linked to each other,
$R^{b1}$ is $R^s$,
$R^{b2}$ is a hydrogen atom or $R^s$,
$R^{b3}$ is a hydrogen atom or $R^s$, or
two or three of $R^{b1}$, $R^{b2}$, and $R^{b3}$, taken together with the adjacent carbon atom, may form a cyclic group optionally having one or more substituents, and
$R^s$, in each occurrence, is the same or different and represents a hydrocarbon group optionally having one or more substituents (in the present specification, this compound may be referred to as "compound (1)"),
the method comprising
step A of reacting a compound represented by formula (2):

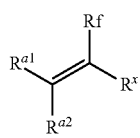

(2)

wherein
$R^x$ is a leaving group, and
other symbols are as defined above (in the present specification, this compound may be referred to as "compound (2)"), with a compound represented by formula (3):

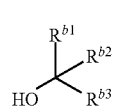

(3)

wherein the symbols in the formula are as defined above (in the present specification, this compound may be referred to as "compound (3)")
in the presence of a transition metal catalyst.

The structure of the divalent group formed by linking (i) $R^{a1}$ and $R^{a2}$, (ii) $R^{a1}$ and Rf, or (iii) Rf and $R^{a2}$ is understood based on each structure of $R^{a1}$, $R^{a2}$, and Rf.

Each linkage between (i) $R^{a1}$ and $R^{a2}$, (ii) $R^{a1}$ and Rf, and (iii) Rf and $R^{a2}$, may be made internally or at the end of each group.

$R^{a1}$ is preferably a hydrogen atom, an alkyl group, an aryl group, a heterocyclic group, an alkoxy group, an alkoxycarbonyl group, a carbamoyl group, an amino group, or a cyano group.

$R^{a1}$ is more preferably a hydrogen atom, an alkyl group, an aryl group, a heterocyclic group, or an alkoxy group.

$R^{a1}$ is still more preferably a hydrogen atom or an aryl group.

$R^{a1}$ is even more preferably a hydrogen atom or a $C_{6-14}$ aryl group.

$R^{a2}$ is preferably a hydrogen atom, an alkyl group, an aryl group, a heterocyclic group, an alkoxy group, an alkoxycarbonyl group, a carbamoyl group, an amino group, or a cyano group.

$R^{a2}$ is more preferably an alkyl group, an aryl group, a heterocyclic group, or an alkoxy group.

$R^{a2}$ is still more preferably a hydrogen atom or an aryl group.

$R^{a2}$ is even more preferably a hydrogen atom or a $C_{6-14}$ aryl group.

$R^{a2}$ is particularly preferably a hydrogen atom.

It is preferable that
$R^{b1}$ be
(1) an alkyl group optionally having one or more substituents (preferably, —OH, —SH, and —NH$_2$ can be excluded from the substituents),
(2) a cycloalkyl group optionally having one or more substituents,
(3) an aryl group optionally having one or more substituents, or
(4) a heterocyclic group optionally having one or more substituents (examples of the substituents include halogeno groups and alkyl groups);
$R^{b2}$ be
(1) a hydrogen atom or
(2) an alkyl group optionally having one or more substituents (examples of the substituents include halogeno groups), and
$R^{b3}$ be
(1) a hydrogen atom or
(2) an alkyl group optionally having one or more substituents (examples of the substituents include halogeno groups),
or
two or three of $R^{b1}$, $R^{b2}$, and $R^{b3}$, taken together, may form an aromatic hydrocarbon ring optionally substituted with one or more alkyl groups.

It is more preferable that
$R^{b1}$ be
an alkyl group optionally having one or more substituents selected from the group consisting of halogeno, aryl, and heteroaryl groups,
$R^{b2}$ be
(1) a hydrogen atom or
(2) an alkyl group optionally having one or more substituents (examples of the substituents include halogeno groups), and
$R^{b3}$ be
a hydrogen atom,
or
two or three of $R^{b1}$, $R^{b2}$, and $R^{b3}$, taken together, may form a $C_{6-14}$ aromatic hydrocarbon ring optionally substituted with one or more $C_{1-11}$ alkyl groups.

It is still more preferable that
$R^{b1}$ be a $C_{1-11}$ alkyl group optionally having one or more substituents selected from the group consisting of fluoro, $C_{6-14}$ aryl, and 5- to 18-membered heteroaryl groups,
$R^{b2}$ be a hydrogen atom, and
$R^{b3}$ be a hydrogen atom,
or
two or three of $R^{b1}$, $R^{b2}$, and $R^{b3}$, taken together, may form a $C_{6-14}$ aromatic hydrocarbon ring optionally substituted with one or more $C_{1-11}$ alkyl groups.

It is even more preferable that
$R^{b1}$ be a $C_{1-11}$ fluoroalkyl group (preferably a $C_{1-11}$ linear perfluoroalkyl group),
$R^{b2}$ be a hydrogen atom, and
$R^{b3}$ be a hydrogen atom.

It is preferable that
$R^{a1}$ be a hydrogen atom, an alkyl group, a halogeno group, an aryl group, a heterocyclic group, an alkoxy group, an alkoxycarbonyl group, a carbamoyl group, an amino group, an amide group, a cyano group, a nitro group, a sulfonyl group, or a sulfide group, $R^{a2}$ be a hydrogen atom, an alkyl group, a halogeno group, an aryl group, a heterocyclic group, an alkoxy group, an alkoxycarbonyl group, a carbamoyl group, an amino group, an amide group, a cyano group, a nitro group, a sulfonyl group, or a sulfide group,
$R^{b1}$ be
(1) a hydrogen atom,
(2) an alkyl group optionally having one or more substituents,
(3) a cycloalkyl group optionally having one or more substituents,
(4) an aryl group optionally having one or more substituents, or
(5) a heterocyclic group optionally having one or more substituents,
$R^{b2}$ be
(1) a hydrogen atom,
(2) an alkyl group optionally having one or more substituents,
(3) a cycloalkyl group optionally having one or more substituents,
(4) an aryl group optionally having one or more substituents, or
(5) a heterocyclic group optionally having one or more substituents,
$R^{b3}$ be
(1) a hydrogen atom,
(2) an alkyl group optionally having one or more substituents,
(3) a cycloalkyl group optionally having one or more substituents,
(4) an aryl group optionally having one or more substituents, or
(5) a heterocyclic group optionally having one or more substituents,
or
two or three of $R^{b1}$, $R^{b2}$, and $R^{b3}$, taken together, form an aliphatic hydrocarbon ring optionally having one or more substituents, or an aromatic hydrocarbon ring optionally having one or more substituents.

It is more preferable that
$R^{a1}$ be a hydrogen atom, an alkyl group, an aryl group, a heterocyclic group, or an alkoxy group,
$R^{a2}$ be a hydrogen atom, an alkyl group, an aryl group, a heterocyclic group, or an alkoxy group,
$R^{b1}$ be
(2) a $C_{1-20}$ linear or $C_3$-20 branched alkyl group optionally having one or more substituents,
(3) a $C_{3-20}$ cycloalkyl group optionally having one or more substituents,
(4) a $C_{5-20}$ aryl group optionally having one or more substituents, or
(5) a $C_{5-20}$ heterocyclic group optionally having one or more substituents,
$R^{b2}$ be
(1) a hydrogen atom,
(2) a $C_{1-20}$ linear or $C_{3-20}$ branched alkyl group optionally having one or more substituents,
(3) a $C_{3-20}$ cycloalkyl group optionally having one or more substituents,
(4) a $C_{5-20}$ aryl group optionally having one or more substituents, or
(5) a $C_{5-20}$ heterocyclic group optionally having one or more substituents,
$R^{b3}$ be
(1) a hydrogen atom,
(2) a $C_{1-20}$ linear or $C_{3-20}$ branched alkyl group optionally having one or more substituents,
(3) a $C_{3-20}$ cycloalkyl group optionally having one or more substituents,
(4) a $C_{5-20}$ aryl group optionally having one or more substituents,
or
(5) a $C_{5-20}$ heterocyclic group optionally having one or more substituents, or
two or three of $R^{b1}$, $R^{b2}$, and $R^{b3}$, taken together with the adjacent carbon atom, form a $C_{3-18}$ aliphatic hydrocarbon ring optionally substituted with one or more $C_{1-11}$ alkyl groups, or a $C_{5-14}$ aromatic hydrocarbon ring optionally substituted with one or more $C_{1-11}$ alkyl groups.

It is still more preferable that
$R^{a1}$ be a hydrogen atom, an alkyl group, a halogeno group, or an aryl group,
$R^{a2}$ be a hydrogen atom, an alkyl group, a halogeno group, or an aryl group,
$R^{b1}$ be
(1) a hydrogen atom,
(2) $C_{1-11}$ linear or $C_{3-11}$ branched alkyl group, optionally having one or more substituents,
(3) a $C_{1-11}$ cycloalkyl group optionally having one or more substituents,
(4) a $C_{5-11}$ aryl group optionally having one or more substituents, or
(5) a $C_{5-11}$ heterocyclic group optionally having one or more substituents, $R^{b2}$ be
(1) a hydrogen atom,
(2) a $C_{1-11}$ linear or $C_{3-11}$ branched alkyl group optionally having one or more substituents,
(3) a $C_{1-11}$ cycloalkyl group optionally having one or more substituents,
(4) a $C_{5-11}$ aryl group optionally having one or more substituents,
or
(5) a $C_{5-11}$ heterocyclic group optionally having one or more substituents,
$R^{b3}$ be
(1) a hydrogen atom,
(2) a $C_{1-11}$ linear or $C_{3-11}$ branched alkyl group optionally having one or more substituents,
(3) a $C_{1-11}$ cycloalkyl group optionally having one or more substituents,
(4) a $C_{5-11}$ aryl group optionally having one or more substituents,
or
(5) a $C_{5-11}$ heterocyclic group optionally having one or more substituents, or
two or three of $R^{b1}$, $R^{b2}$, and $R^{b3}$, taken together with the adjacent carbon atom, form a $C_{3-15}$ aliphatic hydrocarbon ring or $C_{5-11}$ aromatic hydrocarbon ring, each optionally having one or more substituents selected from the group consisting of $C_{1-11}$ alkyl and nitro groups.

It is preferable that
$R^{b1}$ be
a $C_{1-11}$ alkyl group optionally having one or more substituents selected from the group consisting of $C_{6-14}$ aryl and 5- to 18-membered heterocyclic groups (e.g., 5- to 18-membered non-aromatic heterocyclic groups and 5- to 18-membered heteroaryl groups), each optionally having one or more substituents selected from the group consisting of fluoro, keto, hydroxy, fluorovinyloxy (e.g., 1-fluorovinyloxy), ether (e.g., $C_{2-11}$ polyether), alkoxycarbonyl, nitro, and trialkylsilyl groups,
$R^{b2}$ be a hydrogen atom, and
$R^{b3}$ be a hydrogen atom, or
two or three of $R^{b1}$, $R^{b2}$, and $R^{b3}$, taken together with the adjacent carbon atom, form a $C_{6-14}$ aromatic hydrocarbon ring optionally having one or more substituents selected from the group consisting of $C_{1-11}$ alkyl and nitro groups.

It is more preferable that
$R^{a1}$ be a hydrogen atom,
$R^{a2}$ be a hydrogen atom
$R^{b1}$ be a hydrogen atom,
$R^{b2}$ be a hydrogen atom, and
$R^{b3}$ be a $C_{1-11}$ linear perfluoroalkyl group.
$R^{x}$ is preferably a halogeno group or a sulfonic acid ester group.

Examples of "sulfonic acid ester group" for $R^{x}$ include methanesulfonyloxy (OMs), benzenesulfonyloxy, p-toluenesulfonyloxy (OTs), trifluoromethanesulfonyloxy (OTf), and nonafluorobutanesulfonyloxy.

$R^{x}$ can be more preferably a halogeno group, a mesyl group, a tosyl group, a nosyl group, a fluorosulfonyl group, a nitro group, or a cyano group.

$R^{x}$ can be more preferably a chloro group or a bromo group.

Both $R^{a1}$ and $R^{a2}$ are preferably hydrogen atoms in order to obtain the effect of the present invention.

Transition Metal Catalyst
Preferable examples of transition metals in transition metal catalysts for use in the present invention include copper, silver, gold, nickel, palladium, platinum, cobalt, rhodium, iridium, iron, ruthenium, manganese, chromium, and zirconium.

Specifically, preferable examples of the transition metal catalyst used in step A include copper catalysts, silver catalysts, gold catalysts, nickel catalysts, palladium catalysts, platinum catalysts, cobalt catalysts, rhodium catalysts, iridium catalysts, iron catalysts, ruthenium catalysts, manganese catalysts, chromium catalysts, and zirconium catalysts.

More preferable examples of transition metals in transition metal catalysts for use in the present invention include palladium, copper, silver, nickel, platinum, cobalt, and iron.

Even more preferable examples of transition metals in transition metal catalysts for use in the present invention include palladium, copper, nickel, platinum, and iron.

Particularly preferable examples of transition metals in transition metal catalysts for use in the present invention include palladium.

That is, particularly preferable examples of the transition metal catalyst for use in the present invention include palladium catalysts.

Examples of palladium catalysts for use in the present invention include
(1) zerovalent palladium complexes;
(2) zerovalent palladium complexes generated from monovalent or divalent palladium complexes during a reaction; and
(3) complexes obtained by mixing these palladium complexes with at least one compound (ligand) selected from the group consisting of ketones, diketones, phosphines, diamines, bipyridines, and phenanthrolines.

In the present specification, specific examples of zerovalent palladium complexes include $Pd_2(dba)_3$ (dba is dibenzylideneacetone), $Pd_2(dba)_3$-$CHCl_3$, $Pd(dba)_2$, $Pd(cod)_2$ (cod is cycloocta-1,5-diene), $Pd(dppe)_2$ (dppe is 1,2-bis(diphenylphosphino) ethane), $Pd(PCy_3)_2$ (Cy is cyclohexyl), $Pd(Pt\text{-}Bu_3)_2$ (t-Bu is t-butyl), $Pd(PPh_3)_4$ (Ph is phenyl), and tris{tris[3,5-bis(trifluoromethyl)phenyl]phosphine}palladium (0).

In the present specification, examples of monovalent palladium complexes include palladium complexes represented by the following chemical formula:

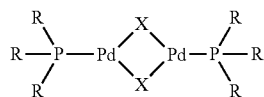

wherein
X is a chlorine atom, a bromine atom, or an iodine atom,
R, in each occurrence, is the same or different and represents a $C_{1-20}$ alkyl group, a $C_{2-20}$ alkenyl group, a $C_{2-20}$ alkynyl group, or an aryl group.

Of these, preferable specific examples include di-μ-chlorobis(tri-tert-butylphosphine)dipalladium (I), di-μ-bromobis(tri-tert-butylphosphine)dipalladium (I), di-μ-iodobis(tri-tert-butylphosphine)dipalladium (I), di-μ-chlorobis{tri(1-adamantyl)phosphine}dipalladium (I), di-μ-bromobis{tri(1-adamantyl)phosphine}dipalladium (I), and di-μ-iodobis{tri(1-adamantyl)phosphine}dipalladium (I).

In the present specification, specific examples of divalent palladium complexes include (1) palladium chloride, palladium bromide, palladium acetate, bis(acetylacetonato)palladium (II), dichloro(η⁴-1,5-cyclooctadiene)palladium (II), dibromo(η⁴-1,5-cyclooctadiene) palladium (II), bis(acetonitrile)dichloropalladium (II), bis(benzonitrile)dichloropalladium (II), and di-μ-chlorobis{(q-allyl)palladium} (II); and (2) complexes obtained by binding a phosphine ligand, such as triphenylphosphine, to these complexes.

These divalent palladium complexes are, for example, reduced by a reducing species (e.g., phosphines, reducing agents, and organic metal reagents) that is co-present during a reaction, thereby generating zerovalent palladium complexes.

The above zerovalent palladium complexes or zerovalent palladium complexes generated from monovalent or divalent palladium complexes through reduction can interact with a compound (ligand), such as ketones, diketones, phosphines, diamines, bipyridines, and phenanthrolines optionally added during a reaction, and can be converted into zerovalent palladium complexes that are involved in the reaction.

It is not always necessary to know how many ligands are bound to a zerovalent palladium complex during the reaction.

Using the above ligands, these palladium complexes are often formed into a homogeneous solution with a reaction substrate to be used in the reaction. In addition, these palladium complexes can also be used as a heterogeneous catalyst dispersed or supported in a polymer such as polystyrene and polyethylene.

Such heterogeneous catalysts have an advantage in processes such as a catalyst recovering process.

Specific examples of catalyst structures thereof include those in which a metal atom is immobilized by a polymeric phosphine or the like that is a crosslinked polystyrene (PS) polymer chain having phosphine introduced thereto, as shown in the following chemical formula.

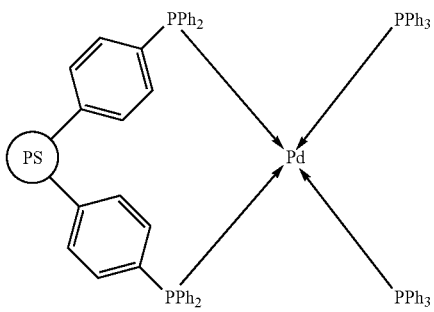

The "palladium catalyst" for use in the present invention may be supported on a carrier.

Such a supported catalyst has a cost advantage because the catalyst can be recycled.

Examples of carriers include carbon, alumina, silica gel-alumina, silica gel, barium carbonate, barium sulfate, calcium carbonate, titanium oxide, zirconium oxide, calcium fluoride, and zeolite.

In addition, the polymeric phosphines disclosed in the following documents can also be used.

1) Kanbara et al., Macromolecules, 2000, vol. 33, p. 657
2) Yamamoto et al., J. Polym. Sci., 2002, vol. 40, p. 2637
3) JPH06-032763 Å
4) JP2005-281454A
5) JP2009-527352A Examples of ketones as the ligands include dibenzylideneacetone.

Examples of diketones as the ligand include β-diketones, such as acetylacetone, 1-phenyl-1,3-butanedione, 1,3-diphenylpropanedione, and hexafluoroacetylacetone.

Preferable examples of phosphines as the ligand include dialkylmonoaryl phosphines, diarylmonoalkyl phosphines, trialkylphosphines, triarylphosphines, and bidentate diphosphines.

Specific examples of dialkylmonoaryl phosphines include diisopropylphenyl phosphine, diisopropyl(o-tolyl) phosphine, diisopropyl(2,6-dimethylphenyl)phosphine, diisopropyl pentafluorophenyl phosphine, di-n-butylphenyl phosphine, di-n-butyl(o-tolyl)phosphine, di-n-butyl(2,6-dimethylphenyl)phosphine, di-n-butyl pentafluorophenyl phosphine, di-tert-butylphenyl phosphine, di-tert-butyl(o-tolyl)phosphine, di-tert-butyl(2,6-dimethylphenyl)phosphine, di-tert-butyl pentafluorophenyl phosphine, dicyclohexyl phenylphosphine, dicyclohexyl(o-tolyl)phosphine, dicyclohexyl(2,6-dimethylphenyl)phosphine, dicyclohexyl pentafluorophenyl phosphine, di(1-adamantyl)phenylphosphine, di(1-adamantyl) (o-tolyl)phosphine, di(1-adamantyl)(2,6-dimethylphenyl)phosphine, di(1-adamantyl)pentafluorophenyl phosphine, 2-dicyclohexylphosphino-2',6'-diisopropoxybiphenyl, 2-dicyclohexylphosphino-2',6'-dimethoxybiphenyl, 2-dicyclohexylphosphino-2',4',6'-triisopropylbiphenyl, 2-dicyclohexylphosphino-2'-(N,N-dimethylamino)biphenyl, 2-(dicyclohexylphosphino)-3,6-dimethoxy-2', 4',6'-triisopropyl-1,1'-biphenyl, 2'-dicyclohexylphosphino-2,4,6-trimethoxybiphenyl, 2-dicyclohexylphosphino-2'-methylbiphenyl, 2-di-tert-butylphosphino-2'-methylbiphenyl, 2-di-tert-butylphosphino-2'-(N,N-dimethylamino)biphenyl, 2-di-tert-butylphosphino-3,4,5,6-tetramethyl-2',4',6'-triisopropyl-1,1'-biphenyl, 2-(di-tert-butylphosphino)-2',4',6'-triisopropyl-3,6-dimethoxy-1,1'-biphenyl, 2-di-tert-butylphosphino-2',4',6'-triisopropylbiphenyl, (2-biphenyl)dicyclohexylphosphine, (2-biphenyl)di-tert-butylphosphine, (3R, 5R)-adamantan-1-yl ((3S,5-adamantan-1-yl) ((3S,5-adamantan-1-yl)) (2',4',6'-triisopropyl-3,6-dimethoxy-(1,1'-biphenyl)-2-yl)phosphine, 2'-di-tert-butylphosphino)-3-methoxy-6-methyl-(2',4',6'-triisopropyl-1,1'-biphenyl, and 2-(di-t-butylphosphino)-3-methoxy-6-methyl-2',4',6'-tri-i-propyl-1,1'-biphenyl.

Specific examples of diarylmonoalkyl phosphines include diphenylmethylphosphine, diphenylisopropylphosphine, n-butyl diphenylphosphine, tert-butyl diphenylphosphine, cyclohexyl diphenylphosphine, (1-adamantyl)diphenylphosphine, di(o-tolyl)methylphosphine, di(o-tolyl)isopropylphosphine, n-butyldi(o-tolyl)phosphine, tert-butyldi(o-tolyl)phosphine, cyclohexyldi(o-tolyl)phosphine, (1-adamantyl)di(o-tolyl)phosphine, bis(2,6-dimethylphenyl)methylphosphine, bis(2,6-dimethylphenyl)isopropylphosphine, bis(2,6-dimethylphenyl)-n-butylphosphine, bis(2,6-dimethylphenyl)-tert-butylphosphine, bis(2,6-dimethylphenyl)cyclohexylphosphine, (1-adamantyl)bis(2,6-dimethylphenyl)phosphine, bis(pentafluorophenyl)methylphosphine, bis(pentafluorophenyl)isopropylphosphine, bis(pentafluorophenyl)-n-butylphosphine, bis(pentafluorophenyl)-tert-butylphosphine, bis(pentafluorophenyl)cyclohexylphosphine, and (1-adamantyl)bis(pentafluorophenyl) phosphine.

Specific examples of trialkylphosphines include tri($C_{3-20}$ alkyl)phosphines, such as tricyclohexylphosphine, triisopropylphosphine, tri-tert-butylphosphine, trihexylphosphine, tri (1-adamantyl)phosphine, tricyclopentylphosphine, di-tert-butyl methylphosphine, cyclohexyldi-tert-butylphosphine, di-tert-butyl neopentylphosphine, di-tert-butyl isopropylphosphine, di-tert-butyl(2-butenyl)phosphine, di-tert-butyl (3-methyl-2-butenyl)phosphine, 1-adamantyl-di-tert-butylphosphine, tert-butyldi(1-adamantyl)phosphine, di(1-adamantyl)isopropylphosphine, cyclohexyldi(1-adamantyl)phosphine, n-butyldi(1-adamantyl)phosphine, tribicyclo[2,2,2]octylphosphine, and trinorbornyl phosphine.

Specific examples of triarylphosphines include tri(monocyclic aryl)phosphines, such as triphenylphosphine, trimesitylphosphine, tri(o-tolyl)phosphine, tris{(4-trifluoromethyl)phenyl}phosphine, tris(pentafluorophenyl)phosphine, and tris[3,5-bis(trifluoromethyl)phenyl]phosphine.

Specific examples of bidentate diphosphines include 1,2-bis(diphenylphosphino)ethane, 1,3-bis(diphenylphosphino)propane, 1,4-bis(diphenylphosphino)butane, 1,5-bis(diphenylphosphino)pentane, 1,3-bis(diisopropylphosphino)propane, 1,4-bis(diisopropylphosphino)butane, 1,3-bis(dicyclohexylphosphino)propane, 1,4-bis(dicyclohexylphosphino)butane, bis(diphenylphosphinophenyl)ether, bis(dicyclohexylphosphinophenyl)ether, 1,1'-bis(diphenylphosphino)ferrocene, 1,1'-bis(dicyclohexylphosphino)ferrocene, 1,1'-bis(diisopropylphosphino)ferrocene, 1,1'-bis(di-tert-butylphosphino)ferrocene, 1,2-bis(di-tert-butylphosphinomethyl)benzene, 4,6-bis(diphenylphosphino)phenoxazine, 4,5-bis(diphenylphosphino)-9,9'-dimethylxanthene, 4,5-bis(di-tert-butylphosphino)-9,9'-dimethylxanthene, and 2,2'-bis(diphenylphosphino)-1,1'-binaphthyl.

The transition metal catalysts for use in the present invention may be used alone, or in a combination of two or more.

The phosphines used in the present invention may be tetrafluoro borates (e.g., trialkylphosphonium tetrafluoroborates, such as trihexylphosphonium tetrafluoroborate and tri-tert-butyl phosphonium tetrafluoroborate).

Such a salt can be reacted with a base described in detail below to give a free body of phosphine (e.g., trialkylphosphine, such as tricyclohexylphosphine and tri-tert-butylphosphine).

The phosphines used in the present invention may be in oxide form.

Examples of the oxide form include di(cyclo)alkylphosphine oxides (e.g., di-tert-butylphosphine oxide and di(1-adamantyl)phosphine oxide).

Arylphosphines for heterogeneous catalysts, in which a phosphine unit is introduced into a polymer chain, can also be preferably used.

Specific examples thereof include a triarylphosphine formed by binding one of the phenyl groups of triphenylphosphine to a polymer chain, as shown in the chemical formula below:

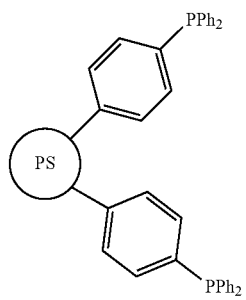

Examples of diamines include tetramethylethylenediamine and 1,2-diphenylethylenediamine.

Examples of bipyridines include 2,2'-bipyridyl, 4,4'-dimethyl-2,2'-bipyridyl, 5,5'-dimethyl-2,2'-bipyridyl, 6,6'-dimethyl-2,2'-bipyridyl, 4,4'-di-tert-butyl-2,2'-bipyridine, 4,4'-dimethoxy-2,2'-bipyridyl, 2,2'-biquinoline, α,α',α''-tripyridyl.

Examples of phenanthrolines include 1,10-phenanthroline, 2-methyl-1,10-phenanthroline, 3-methyl-1,10-phenanthroline, 5-methyl-1,10-phenanthroline, 2,9-dimethyl-1,10-phenanthroline, 2,9-diphenyl-1,10-phenanthroline, 4,7-dimethyl-1,10-phenanthroline, 5,6-dimethyl-1,10-phenanthroline, 4,7-diphenyl-1,10-phenanthroline, 2,9-dimethyl-4,7-diphenyl-1,10-phenanthroline, 3,4,7,8-tetramethyl-1,10-phenanthroline.

Preferred examples of the ligands include phosphines, diamines, bipyridines, and phenanthrolines.

More preferable examples of the ligands include triarylphosphines and trialkylphosphines.

Preferred examples of triarylphosphines include triphenylphosphine and tris[3,5-bis(trifluoromethyl)phenyl]phosphine.

Preferred examples of trialkylphosphines include tricyclohexylphosphine, tri-tert-butylphosphine, triisopropylphosphine, and tri(1-adamantyl)phosphine.

Preferred examples thereof also include a triarylphosphine formed by binding one of the phenyl groups of triphenylphosphine to a polymer chain as described above.

The palladium catalyst is preferably tris(benzylideneacetone) dipalladium or bis(benzylideneacetone) palladium.

Coordination Compound

The reaction of step A can preferably be performed in the presence of a coordination compound.

That is, the reaction of step A can be preferably performed in the presence of the transition metal catalyst mentioned above, and a coordination compound.

The coordination compound used in step A is a compound capable of forming a coordinate bond with the transition metal catalyst (e.g., palladium).

Examples of the coordination compound include the examples of the ligand mentioned above.

The coordination compound is particularly preferably a biphenyl compound represented by formula (4-1):

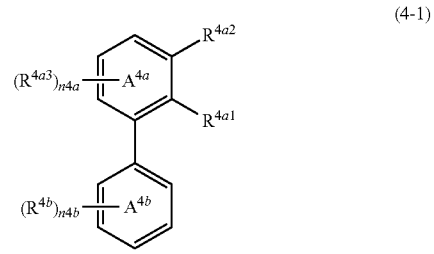

wherein
$A^4$ is a benzene ring,
$A^{4b}$ is a benzene ring,
$R^{4a1}$ is a phosphino group substituted with two $C_{1\text{-}20}$ hydrocarbon groups,
$R^{4a2}$ is an alkyl group or an alkoxy group,
$R^{4a3}$, in each occurrence, is the same or different and represents a substituent,
$R^{4b}$, in each occurrence, is the same or different and represents a substituent,
n4a is a number of 0 to 3, and
n4b is a number of 0 to 5.

$R^{4a1}$ is
preferably a phosphino group substituted with two substituents (which may be the same or different) selected from the group consisting of secondary $C_{1-6}$ alkyl, tertiary $C_{1-6}$ alkyl, and $C_{3-12}$ cycloalkyl groups,
more preferably a phosphino group substituted with two substituents (which may be the same or different) selected from the group consisting of isopropyl, cyclohexyl, tert-butyl, and adamantyl groups,
still more preferably a phosphino group substituted with two substituents (which may be the same or different) selected from the group consisting of cyclohexyl, tert-butyl, and adamantyl groups, and
even more preferably a phosphino group substituted with two substituents (which may be the same or different) selected from the group consisting of tert-butyl and adamantyl groups.

$R^{4a2}$ is
preferably a $C_{1-6}$ alkyl group or a $C_{1-6}$ alkoxy group, more preferably an isopropyl group, a methyl group, an ethyl group, a methoxy group, or an ethoxy group,
still more preferably a methyl group, an ethyl group, a methoxy group, or an ethoxy group, and
even more preferably a methyl group or a methoxy group.

It is preferable that
$R^{4a1}$ be a phosphino group substituted with two substituents selected from the group consisting of cyclohexyl, tert-butyl, and adamantyl groups, and
$R^{4a2}$ be a methyl group or a methoxy group.

$R^{4a3}$, in each occurrence, is the same or different and preferably represents a $C_{1-6}$ alkyl group, a $C_{1-6}$ alkoxy group, or di($C_{1-6}$ alkyl)amino, and
more preferably represents a methyl group, an ethyl group, an isopropyl group, a cyclohexyl group, a tert-butyl group, a methoxy group, an ethoxy group, an isopropoxy group, or a dimethyl amino group.

$R^{4b}$, in each occurrence, is the same or different and represents a substituent,
preferably a $C_{1-6}$ alkyl group, a $C_{1-6}$ alkoxy group, or a di($C_{1-6}$ alkyl)amino, and
more preferably a methyl group, an ethyl group, an isopropyl group, a cyclohexyl group, a tert-butyl group, a methoxy group, an ethoxy group, an isopropoxy group, or a dimethyl amino group.

n4a is
preferably 0 to 3,
more preferably 1 to 2, and
still more preferably 1.

n4b is
preferably 0 to 5,
more preferably 1 to 4, and
still more preferably 2 to 3.

In a preferable embodiment of the present invention,
$A^{4a}$ is a benzene ring,
$A^{4b}$ is a benzene ring,
$R^{4a1}$ is a phosphino group substituted with two identical or different $C_{1-10}$ hydrocarbon groups,
$R^{4a2}$ is a methyl group or a methoxy group,
$R^{4a3}$, in each occurrence, is the same or different and represents a methyl group or a methoxy group,
$R^{4b}$, in each occurrence, is the same or different and represents an isopropyl group,
n4a is a number of 1 to 3, and
n4b is a number of 2 to 3.

In a more preferable embodiment of the present invention,
$A^{4a}$ is a benzene ring,
$A^{4b}$ is a benzene ring,
$R^{4a1}$ is a phosphino group substituted with two substituents (which may be the same or different) selected from the group consisting of secondary $C_{1-6}$ alkyl, tertiary $C_{1-6}$ alkyl, and $C_{3-12}$ cycloalkyl groups,
$R^{4a2}$ is a methyl group or a methoxy group,
$R^{4a3}$, in each occurrence, is the same or different and represents a methyl group or a methoxy group,
$R^{4b}$, in each occurrence, is the same or different and represents an isopropyl group,
n4a is a number of 1 to 3, and
n4b is a number of 2 to 3.

In a still more preferable embodiment of the present invention,
$A^{4a}$ is a benzene ring,
$A^{4b}$ is a benzene ring,
$R^{4a1}$ is a phosphino group substituted with two substituents selected from the group consisting of cyclohexyl, tert-butyl, and adamantyl groups,
$R^{4a2}$ is a methoxy group,
$R^{4a3}$, in each occurrence, is the same or different and represents a methyl group or a methoxy group,
$R^{4b}$, in each occurrence, is the same or different and represents an isopropyl group,
n4a is 1, and
n4b is 3.

Base

The reaction of step A can preferably be performed in the presence of a base.

That is, the reaction of step A can preferably be performed in the presence of the transition metal catalyst mentioned above and a base.

The reaction of step A can preferably be performed in the presence of the transition metal catalyst mentioned above, the coordination compound mentioned above, and a base.

The base is preferably a base having a pKa of preferably 36 to 3.6, more preferably 20 to 5, and even more preferably 12 to 9.

In the present specification, pKa refers to a numerical value determined by performing acid-base titration in water at 25° C. When a basic compound has multiple pKa values, the maximum value is taken as the pKa value of the basic compound.

The base is preferably at least one member selected from the group consisting of
(1) acetates, carbonates, hydrogen carbonates, phosphates, hydrogen phosphates, alkoxide salts, hydroxide salts, hydride salts, ammonium salts, and amide salts of alkaline or alkaline earth metals,
(2) polymer-supported bases,
(3) alkali metals, and
(4) amines.

Examples of the alkoxide salts include sodium methoxide, sodium ethoxide, sodium butoxide, potassium methoxide, potassium ethoxide, potassium butoxide, lithium methoxide, and lithium ethoxide.

Examples of the hydroxide salts include sodium hydroxide, potassium hydroxide, lithium hydroxide, rubidium hydroxide, cesium hydroxide, magnesium hydroxide, calcium hydroxide, and barium hydroxide.

Examples of the hydride salts include sodium hydride, potassium hydride, lithium hydride, and calcium hydride.

Examples of the polymer-supported bases include Amberlite (trade name) resin.

Examples of the alkali metals include sodium, potassium, and lithium.

Examples of the amines include aliphatic amines, alicyclic amines, aromatic amines, and heterocyclic amines. The amines can preferably be tertiary amines.

The base is preferably at least one member selected from the group consisting of sodium hydrogen carbonate, potassium hydrogen carbonate, sodium carbonate, potassium carbonate, cesium carbonate, sodium acetate, potassium acetate, trimethylamine, triethylamine, pyridine, sodium methoxide, potassium methoxide, sodium tert-butoxide, potassium tert-butoxide, lithium hexamethyldisilazide, and lithium diisopropylamide.

The base is particularly preferably cesium carbonate.

The amount of the palladium catalyst used in step A may be preferably 0.001 to 0.3 mol, more preferably 0.002 to 0.1 mol, and even more preferably 0.003 to 0.05 mol, per mole of compound (2).

The target product is efficiently obtained by performing the reaction using a palladium catalyst in this amount range.

The amount of the coordination compound used in step A may be preferably 0.002 to 0.6 mol, more preferably 0.004 to 0.2 mol, and even more preferably 0.006 to 0.1 mol, per mole of compound (2).

The target product is efficiently obtained by performing the reaction using a coordination compound in this amount range.

The amount of the weak base used in step A may be preferably 0.5 to 5 mol, more preferably 1 to 3 mol, and even more preferably 1.2 to 2 mol, per mole of compound (2).

The target product is efficiently obtained by performing the reaction using a weak base in this amount range.

The amount of compound (3) used in step A may be preferably 0.05 to 10 mol, more preferably 0.08 to 5 mol, and even more preferably 0.1 to 2 mol, per mole of compound (2).

The target product is efficiently obtained by performing the reaction using compound (3) in this amount range.

The reaction can be performed in the presence or absence of an inert gas (e.g., nitrogen gas).

The reaction of step A can be performed in the presence of or absence of a solvent.

Examples of the solvent include aprotic solvents.

Examples of the aprotic solvent include aromatic hydrocarbons, such as benzene, toluene, and xylene;
ethers, such as cyclopentyl methyl ether, tetrahydrofuran, bis(2-methoxyethyl)ether, and 1,2-bis(2-methoxyethoxy)ethane; lactams, such as N-methylpyrrolidone;
nitriles, such as acetonitrile and propionitrile;
ketones, such as acetone, ethyl methyl ketone, and isobutyl methyl ketone;
dialkyl sulfoxides, such as dimethyl sulfoxide;
tetraalkylureas, such as 1,3-dimethyl-2-imidazolidinone, dimethylpropyleneurea, and tetramethylurea;
amides, such as N,N-dimethylformamide, N,N-dimethylacetamide, and hexaalkylphosphoric triamide (e.g., hexamethylphosphoric acid amide).

These solvents may be used alone, or in a combination of two or more.

The amount of the solvent for use can be determined to be an amount that is sufficient for the solvent to exhibit its function based on common technical knowledge.

The upper limit of the reaction temperature in step A can be preferably 200° C., more preferably 150° C., and even more preferably 120° C.

The lower limit of the reaction temperature in step A can be preferably 25° C., more preferably 50° C., and even more preferably 90° C.

The reaction temperature in step A can be preferably 25 to 200° C., more preferably 50 to 150° C., and even more preferably 90 to 120° C.

The lower the upper limit of the reaction temperature in step A, the more likely it is that side reactions can be suppressed.

The higher the lower limit of the reaction temperature in step A, the more likely it is that the progress of the desired reaction is promoted.

The upper limit of the reaction time in step A can be preferably 48 hours, more preferably 24 hours, and even more preferably 12 hours.

The lower limit of the reaction time in step A can be preferably 0.5 hours, more preferably 2 hours, and even more preferably 6 hours.

The reaction time in step A can be preferably 0.5 to 48 hours, more preferably 2 to 24 hours, and even more preferably 6 to 12 hours.

The shorter the upper limit of the reaction time in step A, the more likely it is that side reactions can be suppressed.

The longer the lower limit of the reaction time in step A, the more likely it is that the progress of the desired reaction is promoted.

The reaction of step A can be performed in the presence or absence of an inert gas (e.g., nitrogen gas).

The reaction of step A can preferably be performed in the presence of an inert gas (e.g., nitrogen gas).

Step A can be performed under reduced pressure, atmospheric pressure, or increased pressure.

According to the production method of the present invention, the molar yield of the compound (1) with respect to compound (2) can preferably be 50% or more, more preferably 60% or more, even more preferably 70% or more, and still more preferably 80% or more.

The compound (1) obtained in step A can be optionally isolated or purified by a known method, such as extraction, dissolution, concentration, precipitation, dehydration, adsorption, distillation, rectification, or chromatography; or combinations thereof.

2. Compound

Among the compounds that can be produced by the production method of the present invention, the following compounds are novel compounds.

The present invention also provides these compounds. These compounds can be usefully used, for example, as a monomer for polymer production, a pharmaceutical intermediate, or a pesticide intermediate.

2.1. Compound (1-1)

A compound represented by formula (1-1):

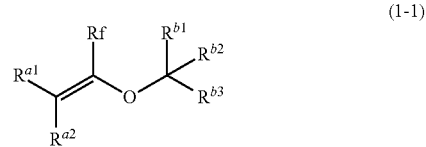

(1-1)

wherein
Rf is a fluoro group or a perfluoroalkyl group,
$R^{a1}$ is a hydrogen atom,
$R^{a2}$ is a hydrogen atom,
$R^{b1}$ is a hydrogen atom,
$R^{b2}$ is a hydrogen atom, and
$R^{b3}$ is a $C_{2-11}$ fluoroalkyl group or a $C_{2-11}$ perfluoroalkyl ether group.

$R^{b3}$ is preferably a $C_{2-11}$ perfluoroalkyl group or a $C_{3-11}$ perfluoroalkylpolyether group, and more preferably a $C_{2-11}$ linear perfluoroalkyl group or $C_{3-11}$ branched perfluoroalkylpolyether group (the polyether group preferably has 2 to 4 ether bonds (—O—)).

2.2. Compound (1-2)

A compound represented by formula (1-2):

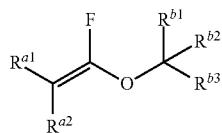
(1-2)

wherein $R^{a1}$ is a hydrogen atom, $R^{a1}$ is a phenyl group, $R^{b1}$ is a hydrogen atom, $R^{b2}$ is a hydrogen atom, and $R^{b3}$ is a $C_{1-11}$ fluoroalkyl group (preferably a $C_{1-11}$ linear perfluoroalkyl group).

The production method according to the present invention is also capable of producing compounds represented by the following formula (1-1b), in addition to the compounds represented by the above formula (1).

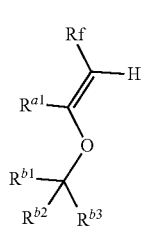
(1-1b)

The symbols in this formula may be as defined for formula (1) above.

Therefore, according to the present invention, a composition comprising a compound represented by formula (1) above and a compound represented by formula (1-1b) above can also be produced.

The molar ratio of the compound represented by formula (1) and the compound represented by formula (1-1b) in the composition may be, for example, 95:5 to 90:10, 80:20 to 65:35, 60:40 to 40:60, and 10:90 to 5:95.

The ratio can be adjusted by setting reaction conditions (e.g., temperature, time).

Further, the ratio can be adjusted by purification after the compound represented by formula (1) and the compound represented by formula (1-1b) are produced.

Among the compounds represented by formula (1-1b), the following compound is a novel compound: a compound represented by:

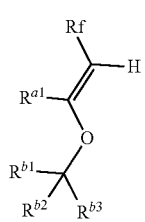
(1-1b)

wherein

Rf is a fluoro group or a perfluoroalkyl group, $R^{a1}$ is a hydrogen atom, $R^{a2}$ is a hydrogen atom, $R^{b1}$ is a hydrogen atom, $R^{b2}$ is a hydrogen atom, and $R^{b3}$ is a $C_{2-11}$ linear perfluoroalkyl group.

The present invention also provides this compound.

EXAMPLES

The present invention is described in more detail below with reference to Examples. However, the present invention is not limited to the Examples.

The meanings of the symbols and abbreviations in the Examples are shown below.

tBuBrettPhos: 2-(di-tert-butylphosphino)-2',4',6'-triisopropyl-3,6-dimethoxy-1,1'-biphenyl BOC: tert-butoxycarbonyl group In the examples, the term "yield" refers to isolated yield, unless otherwise specified.

Example 1

Synthesis of β-fluoro-β-(2,2,2-trifluoroethoxy)styrene

Tris(benzylideneacetone) dipalladium (17.1 mg), 2-(dicyclohexylphosphino)-3,6-dimethoxy-2',4',6'-triisopropyl-1,1'-biphenyl (24.0 mg), β-bromo-β-fluorostyrene (150 mg), and cesium carbonate (365 mg) were placed in a 10-mL two-necked test tube. The container was hermetically sealed and purged with nitrogen.

Toluene (2.3 mL) and 2,2,2-trifluoroethanol (112 mg) were added to the container in a nitrogen atmosphere.

The container was heated at 85° C. for 1.5 hours.

After cooling the container to room temperature, the contents of the container were filtered through Celite with dichloromethane and purified by silica gel column chromatography. The results revealed the production of the target title vinyl ether with a molar yield of 75% with respect to β-bromo-β-fluorostyrene.

Example 2

Synthesis of β-fluoro-β-(2,2,3,3,4,4,5,5,6,6,7,7,7-tridecafluoroheptoxy)styrene

Tris(benzylideneacetone)dipalladium (17.1 mg), 2-(dicyclohexylphosphino)-3,6-dimethoxy-2',4',6'-triisopropyl-1,1'-biphenyl (24.0 mg), β-bromo-β-fluorostyrene (150 mg), 2,2,3,3,4,4,5,5,6,6,7,7,7-tridecafluoroheptan-1-ol (392 mg), and cesium carbonate (365 mg) were placed in a 10-mL two-necked test tube. The container was hermetically sealed and purged with nitrogen.

Toluene (2.3 mL) was added to the container in a nitrogen atmosphere.

The container was heated at 85° C. for 1.5 hours.

After cooling the container to room temperature, the contents of the pressure-resistant container were analyzed by $^{19}$F NMR, which revealed the production of the target title vinyl ether with a molar yield of 78% with respect to β-bromo-β-fluorostyrene (NMR). Further, the contents of the container were filtered through Celite with dichloromethane and purified by silica gel column chromatography. The results revealed the production of the target title vinyl ether with a molar yield of 73% with respect to β-bromo-β-fluorostyrene.

Example 3

Synthesis of β-fluoro-β-(2,2,3,3,4,4,5,5,6,6,7,7,8,8, 9,9,10,10,11,11,11-henicosafluoroundecoxy)styrene Tris(benzylideneacetone)dipalladium (17.1 mg), 2-(dicyclohexylphosphino)-3,6-dimethoxy-2',4',6'-triisopropyl-1,1'-biphenyl (24.0 mg), β-bromo-β-fluorostyrene (150 mg), 2,2,3,3,4,4,5,5,6,6,7,7,8,8,9,9,10,10,11,11,11-henicosafluoroundecan-1-ol (616 mg), and cesium carbonate (365 mg) were placed in a 10-mL two-necked test tube. The container was hermetically sealed and purged with nitrogen.

Toluene (2.3 mL) was added to the container in a nitrogen atmosphere.

The container was heated at 85° C. for 4 hours.

After cooling the container to room temperature, the contents of the pressure-resistant container were analyzed by $^{19}$F NMR, which revealed the production of the target title vinyl ether with a molar yield of 72% with respect to β-bromo-β-fluorostyrene (NMR).

Example 4

Synthesis of 1-fluoro-1-(2',2',2'-trifluoroethoxy) ethylene

Tris(benzylideneacetone)dipalladium (4.6 mg), 2-(di-tert-butylphosphino)-2',4',6'-triisopropyl-3,6-dimethoxy-1,1'-biphenyl (5.8 mg), and cesium carbonate (195 mg) were placed in a 10-mL pressure-resistant container. The container was hermetically sealed and purged with nitrogen.

Toluene (1 mL) and 2,2,2-trifluoroethanol (40 mg) were added to the container in a nitrogen atmosphere.

After cooling the container to −78° C., 1-bromo-1-fluoroethylene (160 mg) was added to the container.

The container was heated at 110° C. for 12 hours.

After cooling the container to room temperature, the contents of the pressure-resistant container were analyzed by $^{19}$F NMR, which revealed the production of the target title vinyl ether with a molar yield of 90% with respect to 2,2,2-trifluoroethanol (NMR).

Example 5

Synthesis of 1,1,1,2,2,3,3,4,4,5,5,6,6,7,7,8,8,9,9,10, 10,11,11,11-henicosafluoro-11-[(1-fluorovinyl)oxy] undecane Tris(benzylideneacetone)dipalladium (4.6 mg), 2-(di-tert-butylphosphino)-2',4',6'-triisopropyl-3,6-dimethoxy-1,1'-biphenyl (5.8 mg), 2,2,3,3,4,4,5,5,6,6,7,7,8,8,9,9,10,10,11,11,11-henicosafluoro-1-undecanol (220 mg), and cesium carbonate (195 mg) were placed in a 10-mL pressure-resistant container. The container was hermetically sealed and purged with nitrogen.

Toluene (1 mL) was added to the container in a nitrogen atmosphere.

After cooling the container to −78° C., 1-bromo-1-fluoroethylene (90 mg) was added to the container.

The container was heated at 110° C. for 12 hours.

After cooling the container to room temperature, the contents of the pressure-resistant container were analyzed by $^{19}$F NMR, which revealed the production of the target title vinyl ether with a molar yield of 80% with respect to 2,2,3,3,4,4,5,5,6,6,7,7,8,8,9,9,10,10,11,11,11-henicosafluoro-1-undecanol (NMR).

Example 6

Synthesis of 1,1,1,2,2,3,3,4,4,5,5,6,6,7,7,8,8,9,9,10, 10,11,11,11-henicosafluoro-li-[(1-fluorovinyl)oxy] undecane Tris(benzylideneacetone)dipalladium (2.2 mg), 2-(di-tert-butylphosphino)-2',4',6'-triisopropyl-3,6-dimethoxy-1,1'-biphenyl (2.9 mg), 2,2,3,3,4,4,5,5,6,6,7,7,8,8,9,9,10,10,11,11,11-henicosafluoro-1-undecanol (220 mg), and cesium carbonate (195 mg) were placed in a 10-mL pressure-resistant container. The container was hermetically sealed and purged with nitrogen.

Toluene (1 mL) was added to the container in a nitrogen atmosphere.

After cooling the container to −78° C., 1-chloro-1-fluoroethylene (230 mg) was added to the container.

The container was heated at 110° C. for 12 hours.

After cooling the container to room temperature, the contents of the pressure-resistant container were analyzed by $^{19}$F NMR, which revealed the production of the target title vinyl ether with a molar yield of 76% with respect to 2,2,3,3,4,4,5,5,6,6,7,7,8,8,9,9,10,10,11,11,11-henicosafluoro-1-undecanol (NMR).

Example 7

Synthesis of 2-(1'-fluorovinyloxy)ethylbenzene

Tris(benzylideneacetone)dipalladium (2.2 mg), 2-(di-tert-butylphosphino)-2',4',6'-triisopropyl-3,6-dimethoxy-1,1'-biphenyl (2.9 mg), phenethyl alcohol (48.9 mg), and cesium carbonate (195 mg) were placed in a 10-mL pressure-resistant container. The container was hermetically sealed and purged with nitrogen.

Toluene (1 mL) was added to the container in a nitrogen atmosphere.

After cooling the container to −78° C., 1-chloro-1-fluoroethylene (270 mg) was added to the container.

The container was heated at 110° C. for 12 hours.

After cooling the container to room temperature, the contents of the pressure-resistant container were analyzed by $^{19}$F NMR, which revealed the production of the target title vinyl ether with a molar yield of 88% with respect to phenethyl alcohol (NMR).

Example 8

Synthesis of 2-(1'-fluorovinyloxy)ethylnaphthalene

Tris(benzylideneacetone)dipalladium (2.2 mg), 2-(di-tert-butylphosphino)-2',4',6'-triisopropyl-3,6-dimethoxy-1,1'-biphenyl (2.9 mg), 2-(1-naphthyl)ethanol (68.9 mg), and cesium carbonate (195 mg) were placed in a 10-mL pressure-resistant container. The container was hermetically sealed and purged with nitrogen.

Toluene (1 mL) was added to the container in a nitrogen atmosphere.

After cooling the container to −78° C., 1-chloro-1-fluoroethylene (200 mg) was added to the container.

The container was heated at 110° C. for 12 hours.

After cooling the container to room temperature, the contents of the pressure-resistant container were analyzed by

Example 9

Synthesis of 1-tert-butyl 4-(1-fluorovinyloxy)benzene

Tris(benzylideneacetone)dipalladium (2.2 mg), 2-(di-tert-butylphosphino)-2',4',6'-triisopropyl-3,6-dimethoxy-1,1'-biphenyl (2.9 mg), 4-tert-butylphenol (60.1 mg), and cesium carbonate (195 mg) were placed in a 10-mL pressure-resistant container. The container was hermetically sealed and purged with nitrogen.

Toluene (1 mL) was added to the container in a nitrogen atmosphere.

After cooling the container to −78° C., 1-chloro-1-fluoroethylene (170 mg) was added to the container.

The container was heated at 110° C. for 12 hours.

After cooling the container to room temperature, the contents of the pressure-resistant container was filtered through Celite with dichloromethane and purified by silica gel column chromatography. The results revealed the production of the desired title vinyl ether with a molar yield of 70% with respect to 4-tert-butylphenol.

Example 10

Synthesis of 4-{(1-fluorovinyloxy)methyl}pyridine

Tris(benzylideneacetone)dipalladium (2.2 mg), 2-(di-tert-butylphosphino)-2',4',6'-triisopropyl-3,6-dimethoxy-1,1'-biphenyl (2.9 mg), 4-pyridinemethanol (43.7 mg), and cesium carbonate (195 mg) were placed in a 10-mL pressure-resistant container. The container was hermetically sealed and purged with nitrogen.

Toluene (1 mL) was added to the container in a nitrogen atmosphere.

After cooling the container to −78° C., 1-chloro-1-fluoroethylene (250 mg) was added to the container.

The container was heated at 110° C. for 12 hours.

After cooling the container to room temperature, the contents of the pressure-resistant container were analyzed by $^{19}$F NMR, which revealed the production of the target title vinyl ether with a molar yield of 75% with respect to 4-pyridinemethanol (NMR).

Example 11

Synthesis of 2-{2-(1-fluorovinyloxy)ethyl}thiophene Tris(benzylideneacetone)dipalladium (2.2 mg), 2-(di-tert-butylphosphino)-2',4',6'-triisopropyl-3,6-dimethoxy-1,1'-biphenyl (2.9 mg), 2-thiophene ethanol (51.3 mg), and cesium carbonate (195 mg) were placed in a 10-mL pressure-resistant container. The container was hermetically sealed and purged with nitrogen.

Toluene (1 mL) was added to the container in a nitrogen atmosphere.

After cooling the container to −78° C., 1-chloro-1-fluoroethylene (270 mg) was added to the container.

The container was heated at 110° C. for 12 hours.

After cooling the container to room temperature, the contents of the pressure-resistant container were analyzed by $^{19}$F NMR, which revealed the production of the target title vinyl ether with a molar yield of 87% with respect to 2-thiophene ethanol (NMR).

Example 12

Synthesis of 1,1,1,2,2,3,3,4,4,5,5,6,6,7,7,8,8,9,9,10,10,11,11,11-henicosafluoro-11-[(1-trifluoromethylvinyl)oxy]undecane Tris(benzylideneacetone)dipalladium (9.2 mg), 2-(di-tert-butylphosphino)-2',4',6'-triisopropyl-3-methoxy-6-methyl-1,1'-biphenyl (11.2 mg), 2,2,3,3,4,4,5,5,6,6,7,7,8,8,9,9,10,10,11,11,11-henicosafluoro-1-undecanol (220 mg), and cesium carbonate (195 mg) were placed in a 10-mL pressure-resistant container. The container was hermetically sealed and purged with nitrogen.

Toluene (1 mL) was added to the container in a nitrogen atmosphere.

After cooling the container to −78° C., 3,3,3-trifluoropropene (210 mg) was added to the container.

The container was heated at 110° C. for 15 hours.

After cooling the container to room temperature, the contents of the pressure-resistant container were analyzed by $^{19}$F NMR, which revealed the production of a mixture of the target title vinyl ether and a regioisomer (mixing ratio=3.3:1) with a molar yield of 24% with respect to 2,2,3,3,4,4,5,5,6,6,7,7,8,8,9,9,10,10,11,11,11-henicosafluoro-1-undecanol (NMR).

Example 13

Synthesis of 2,2,3,3,4,4,5,5-octafluoro-6-((1-fluorovinyl)oxy)hexan-1-ol and 2,2,3,3,4,4,5,5-octafluoro-1,6-bis((1-fluorovinyl)oxy)hexane Tris(benzylideneacetone)dipalladium (2.2 mg), 2-(di-tert-butylphosphino)-2',4',6'-triisopropyl-3,6-dimethoxy-1,1'-biphenyl (2.9 mg), 2,2,3,3,4,4,5,5-octafluoro-1,6-hexanediol (105 mg), and cesium carbonate (195 mg) were placed in a 10-mL pressure-resistant container. The container was hermetically sealed and purged with nitrogen.

Toluene (1 mL) was added to the container in a nitrogen atmosphere.

After cooling the container to −78° C., 1-chloro-1-fluoroethylene (170 mg) was added to the container.

The container was heated at 110° C. for 12 hours.

After cooling the container to room temperature, the contents of the pressure-resistant container were filtered through Celite with dichloromethane and purified by silica gel column chromatography. The results revealed the production of the target title vinyl ethers; i.e., 2,2,3,3,4,4,5,5-octafluoro-6-((1-fluorovinyl)oxy)hexan-1-ol was produced with a molar yield of 25%, and 2,3,3,4,4,5,5-octafluoro-1,6-bis((1-fluorovinyl)oxy)hexane was produced with a molar yield of 30%, with respect to 2,2,3,3,4,4,5,5-octafluoro-1,6-hexanediol.

Example 14

Synthesis of 12-fluoro-2,5,8,11-tetraoxatridec-12-ene Tris(benzylideneacetone)dipalladium (2.2 mg), 2-(di-tert-butylphosphino)-2',4',6'-triisopropyl-3,6-dimethoxy-1,1'-biphenyl (2.9 mg), triethylene glycol monomethyl ether (66 mg), and cesium carbonate (195 mg) were placed in a 10-mL pressure-resistant container. The container was hermetically sealed and purged with nitrogen.

Toluene (1 mL) was added to the container in a nitrogen atmosphere.

After cooling the container to −78° C., 1-chloro-1-fluoroethylene (170 mg) was added to the container.

The container was heated at 110° C. for 12 hours.

After cooling the container to room temperature, the contents of the pressure-resistant container were filtered through Celite with dichloromethane and purified by silica gel column chromatography. The results revealed the production of the target title vinyl ether with a molar yield of 61% with respect to triethylene glycol monomethyl ether.

Example 15

Synthesis of 1-(2-(1-fluorovinyl)oxy)ethyl-4-nitrobenzene Tris(benzylideneacetone)dipalladium (2.2 mg), 2-(di-tert-butylphosphino)-2',4',6'-triisopropyl-3,6-dimethoxy-1,1'-biphenyl (2.9 mg), 4-nitrophenethyl alcohol (66.9 mg), and cesium carbonate (195 mg) were placed in a 10-mL pressure-resistant container. The container was hermetically sealed and purged with nitrogen.

Toluene (1 mL) was added to the container in a nitrogen atmosphere.

After cooling the container to −78° C., 1-chloro-1-fluoroethylene (170 mg) was added to the container.

The container was heated at 110° C. for 12 hours.

After cooling the container to room temperature, the contents of the pressure-resistant container were filtered through Celite with dichloromethane and purified by silica gel column chromatography. The results revealed the production of the target title vinyl ether at a molar yield of 80% with respect to 4-nitrophenethyl alcohol.

Example 16

Synthesis of isobutyl 4-((1-fluorovinyl)oxy)benzoate

Tris(benzylideneacetone)dipalladium (2.2 mg), 2-(di-tert-butylphosphino)-2',4',6'-triisopropyl-3,6-dimethoxy-1,1'-biphenyl (2.9 mg), isoamyl 4-hydroxybenzoate (83.3 mg), and cesium carbonate (195 mg) were placed in a 10-mL pressure-resistant container. The container was hermetically sealed and purged with nitrogen.

Toluene (1 mL) was added to the container in a nitrogen atmosphere.

After cooling the container to −78° C., 1-chloro-1-fluoroethylene (170 mg) was added to the container.

The container was heated at 110° C. for 12 hours.

After cooling the container to room temperature, the contents of the pressure-resistant container were filtered through Celite with dichloromethane and purified by silica gel column chromatography. The results revealed the production of the target title vinyl ether with a molar yield of 30% with respect to isoamyl 4-hydroxybenzoate.

Example 17

Synthesis of N-(3-((1-fluorovinyl)oxy)propyl)phthalimide

Tris(benzylideneacetone)dipalladium (4.6 mg), 2-(di-tert-butylphosphino)-2',4',6'-triisopropyl-3,6-dimethoxy-1,1'-biphenyl (5.8 mg), N-(3-hydroxypropyl)phthalimide (82 mg), and cesium carbonate (195 mg) were placed in a 10-mL pressure-resistant container. The container was hermetically sealed and purged with nitrogen.

Toluene (1 mL) was added to the container in a nitrogen atmosphere.

After cooling the container to −78° C., 1-chloro-1-fluoroethylene (170 mg) was added to the container.

The container was heated at 110° C. for 12 hours.

After cooling the container to room temperature, the contents of the pressure-resistant container were filtered through Celite with dichloromethane and purified by silica gel column chromatography. The results revealed the production of the target title vinyl ether with a molar yield of 60% with respect to N-(3-hydroxypropyl)phthalimide.

Example 18

Synthesis of tert-butyl 4-(((1-fluorovinyl)oxy)methyl)piperidine-1-carboxylate

Tris(benzylideneacetone)dipalladium (2.2 mg), 2-(di-tert-butylphosphino)-2',4',6'-triisopropyl-3,6-dimethoxy-1,1'-biphenyl (2.9 mg), 1-BOC-4-(2-hydroxyethyl)piperidine (91.7 mg), and cesium carbonate (195 mg) were placed in a 10-mL pressure-resistant container. The container was hermetically sealed and purged with nitrogen.

Toluene (1 mL) was added to the container in a nitrogen atmosphere.

After cooling the container to −78° C., 1-chloro-1-fluoroethylene (170 mg) was added to the container.

The container was heated at 110° C. for 12 hours.

After cooling the container to room temperature, the contents of the pressure-resistant container was filtered through Celite with dichloromethane and purified by silica gel column chromatography. The results revealed the production of the target title vinyl ether with a molar yield of 83% with respect to 1-BOC-4-(2-hydroxyethyl)piperidine.

Example 19

Synthesis of tert-butyl(3-((1-fluorovinyl)oxy)propoxy)dimethylsilane

Tris(benzylideneacetone)dipalladium (2.2 mg), 2-(di-tert-butylphosphino)-2',4',6'-triisopropyl-3,6-dimethoxy-1,1'-biphenyl (2.9 mg), 3-[[tert-butyl(dimethyl)silyl]oxy]-1-propanol (76.1 mg), and cesium carbonate (195 mg) were placed in a 10-mL pressure-resistant container. The container was hermetically sealed and purged with nitrogen.

Toluene (1 mL) was added to the container in a nitrogen atmosphere.

After cooling the container to −78° C., 1-chloro-1-fluoroethylene (170 mg) was added to the container.

The container was heated at 110° C. for 12 hours.

After cooling the container to room temperature, the contents of the pressure-resistant container were filtered through Celite with dichloromethane and purified by silica gel column chromatography. The results revealed the production of the target title vinyl ether with a molar yield of 52% with respect to 3-[[tert-butyl(dimethyl)silyl]oxy]-1-propanol.

Example 20

Synthesis of 4-(((1-fluorovinyl)oxy)methyl)-2,2-dimethyl-1,3-dioxolane

Tris(benzylideneacetone)dipalladium (2.2 mg), 2-(di-tert-butylphosphino)-2',4',6'-triisopropyl-3,6-dimethoxy-1,1'-biphenyl (2.9 mg), 1,2-isopropylideneglycerol (52.9 mg), and cesium carbonate (195 mg) were placed in a 10-mL pressure-resistant container. The container was hermetically sealed and purged with nitrogen.

Toluene (1 mL) was added to the container in a nitrogen atmosphere.

After cooling the container to −78° C., 1-chloro-1-fluoroethylene (170 mg) was added to the container.

The container was heated at 110° C. for 12 hours.

After cooling the container to room temperature, the contents of the pressure-resistant container were filtered through Celite with dichloromethane and purified by silica gel column chromatography. The results revealed the production of the target title vinyl ether with a molar yield of 47% with respect to 1,2-isopropylideneglycerol.

Example 21

Synthesis of 1,1,1,2,2,3,3-heptafluoro-3-((1,1,1,2,3,3-hexafluoro-3-(1,1,1,2-tetrafluoro-3-((1-fluorovinyl)oxy)propan-2-yl)oxy)propan-2-yl oxy)propane Tris(benzylideneacetone)dipalladium (11.0 mg), 2-(di-tert-butylphosphino)-2',4',6'-triisopropyl-3,6-dimethoxy-1,1'-biphenyl (14.5 mg), 2,3,3,3-tetrafluoro-2-(1,1,2,3,3,3-hexafluoro-2-(perfluoropropoxy)propoxy)propan-1-ol (480 mg), and cesium carbonate (489 mg) were placed in a 10-mL pressure-resistant container. The container was hermetically sealed and purged with nitrogen.

Toluene (2 mL) was added to the container in a nitrogen atmosphere.

After cooling the container to −78° C., 1-chloro-1-fluoroethylene (612 mg) was added to the container.

The container was heated at 110° C. for 20 hours.

After cooling the container to room temperature, the contents of the pressure-resistant container were filtered through Celite with dichloromethane and analyzed using by $^{19}$F NMR. The results revealed the production of the target title vinyl ether with a molar yield of 70% with respect to 2,3,3,3-tetrafluoro-2-(1,1,2,3,3,3-hexafluoro-2-(perfluoropropoxy)propoxy)propan-1-ol.

Example 22

Synthesis of 1,1,1,2,2,3,3-heptafluoro-3-((1,1,1,2-tetrafluoro-3-((1-fluorovinyl)oxy)propan-2-yl)oxy)propane Tris(benzylideneacetone)dipalladium (11.0 mg), 2-(di-tert-butylphosphino)-2',4',6'-triisopropyl-3,6-dimethoxy-1,1'-biphenyl (14.5 mg), 2,3,3,3-tetrafluoro-2-(perfluoropropoxy)propoxy)propan-1-ol (320 mg), and cesium carbonate (489 mg) were placed in a 10-mL pressure-resistant container. The container was hermetically sealed and purged with nitrogen.

Toluene (2 mL) was added to the container in a nitrogen atmosphere.

After cooling the container to −78° C., 1-chloro-1-fluoroethylene (644 mg) was added to the container.

The container was heated at 110° C. for 20 hours.

After cooling the container to room temperature, the contents of the pressure-resistant container were filtered through Celite with dichloromethane and analyzed by $^{19}$F NMR. The results revealed the production of the target title vinyl ether with a molar yield of 65% with respect to 2,3,3,3-tetrafluoro-2-(perfluoropropoxy)propoxy)propan-1-ol.

The invention claimed is:

1. A compound represented by formula (1-1):

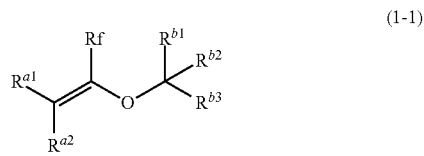

(1-1)

wherein
Rf is a fluoro group or a perfluoroalkyl group,
$R^{a1}$ is a hydrogen atom,
$R^{a2}$ is a hydrogen atom,
$R^{b1}$ is a hydrogen atom,
$R^{b2}$ is a hydrogen atom, and
$R^{b3}$ is a $C_{2-11}$ fluoroalkyl group or a $C_{2-11}$ perfluoroalkylether group.

2. A compound represented by formula (1-2):

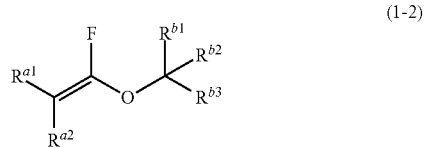

(1-2)

$R^{a1}$ is a hydrogen atom,
$R^{a2}$ is an aryl group or a heterocyclic group,
$R^{b1}$ is a hydrogen atom,
$R^{b2}$ is a hydrogen atom, and
$R^{b3}$ is a $C_{1-11}$ fluoroalkyl group.

3. The compound according to claim 1, wherein $R^{b3}$ is a $C_{2-11}$ perfluoroalkyl group or a $C_{3-11}$ perfluoroalkylpolyether group.

4. The compound according to claim 1, wherein $R^{b3}$ is a $C_{2-11}$ linear perfluoroalkyl group or $C_{3-11}$ branched perfluoroalkylpolyether group.

5. The compound according to claim 4, wherein the polyether group has 2 to 4 ether bonds.

6. The compound according to claim 2, wherein $R^{b3}$ is a $C_{1-11}$ linear fluoroalkyl group.

* * * * *